(12) United States Patent
Theeuwes et al.

(10) Patent No.: US 6,638,263 B1
(45) Date of Patent: Oct. 28, 2003

(54) REGULATION OF DRUG DELIVERY THROUGH FLOW DIVERSION

(75) Inventors: Felix Theeuwes, Los Altos Hills, CA (US); James E. Brown, Los Gatos, CA (US)

(73) Assignee: Durect Corporation, Cupertino, CA (US)

( * ) Notice: Subject to any disclaimer, the term of this patent is extended or adjusted under 35 U.S.C. 154(b) by 0 days.

(21) Appl. No.: 09/416,379

(22) Filed: Oct. 12, 1999

(51) Int. Cl.⁷ .................. A61M 31/00; A61M 5/00; A61M 25/00
(52) U.S. Cl. .................. 604/500; 604/246; 604/523
(58) Field of Search .................. 604/167.01–167.05, 604/256, 264, 27, 500, 523, 508, 511, 515, 516, 517, 521, 246–250; 137/625, 625.47, 872, 874, 861–864

(56) References Cited

U.S. PATENT DOCUMENTS

| | | |
|---|---|---|
| 3,648,694 A | 3/1972 | Mogos et al. |
| 3,949,744 A | 4/1976 | Clarke |
| 4,299,220 A | 11/1981 | Dorman |
| 4,350,155 A | 9/1982 | Thompson |
| 4,360,019 A | 11/1982 | Portner et al. |
| 4,525,165 A | 6/1985 | Fischell |
| 4,544,371 A | 10/1985 | Dormandy, Jr. et al. |
| 4,562,829 A | 1/1986 | Bergner |
| 4,585,941 A | 4/1986 | Bergner |
| 4,692,147 A | 9/1987 | Duggan |
| 4,718,893 A | 1/1988 | Dorman et al. |
| 4,781,672 A | 11/1988 | Hooven |
| 5,088,983 A | 2/1992 | Burke |
| 5,466,228 A * | 11/1995 | Evans ............ 604/248 |
| 5,697,153 A | 12/1997 | Saaski et al. |
| 5,702,618 A | 12/1997 | Saaski et al. |
| 5,800,408 A * | 9/1998 | Strauss et al. ......... 604/264 |
| 5,820,589 A | 10/1998 | Torgerson et al. |
| 5,897,096 A | 4/1999 | Nakano |
| 5,927,951 A * | 7/1999 | Tamari ............ 417/63 |
| 6,158,467 A * | 12/2000 | Loo ............... 137/625.47 |

FOREIGN PATENT DOCUMENTS

| | | |
|---|---|---|
| EP | 0 409 511 B1 | 7/1990 |
| WO | WO 99/38552 | 8/1999 |

* cited by examiner

*Primary Examiner*—Michael J. Hayes
(74) *Attorney, Agent, or Firm*—Carol L. Francis; Bozicevic, Field & Francis LLP; Adam Bell

(57) ABSTRACT

The present invention features methods and devices for modulating the rate of delivery of a drug formulation from a drug delivery device by diverting drug away from a drug delivery pathway. In one embodiment, a flow regulator is positioned relative to a drug delivery pathway of a drug delivery system so that adjustment of the flow regulator can provide for diversion of drug away from the drug delivery pathway. Diverted drug can be either delivered into the systemic circulation of the subject, or can be captured in a waste reservoir.

38 Claims, 12 Drawing Sheets

US 6,638,263 B1

REGULATION OF DRUG DELIVERY THROUGH FLOW DIVERSION

FIELD OF THE INVENTION

This invention relates generally to catheters for use in delivery of drug, particularly in the context of site-specific drug delivery.

BACKGROUND OF THE INVENTION

Many diseases or indications require long term, chronic delivery of drugs or agents to a patient, e.g., cancer, arthritis, heart disease, etc. Long term delivery of drugs or agents can be accomplished by use of drug delivery systems comprising drug delivery devices which may be implanted in a patient's body or retained externally. Drug delivery systems can also deliver drugs or agents to a targeted site within the body via catheters attached to drug delivery devices with the distal end of such catheters placed at the desired site of delivery in the body, with the catheter acting a conduit for the drug or desired agent from the drug delivery device to the desired site of delivery in the body. Drug delivery devices which have adjustable drug delivery rates are known in the art (see, e.g., U.S. Pat. No. 4,692,147). However, such devices with variable or programmable drug delivery rates often include complex mechanical elements which may make such drug delivery devices bulky and subject to failure. Constant drug delivery devices provide for delivery of drug at a preselected, substantially non-fluctuating rate, thus providing for predictability of the dose delivered. However, constant drug delivery devices have the limitation that the rate of drug or agent delivered cannot be readily adjusted, particularly where the drug delivery device is implanted in the body. The ability to readily alter the rate at which drug is administered is often desirable in that it provides flexibility in a therapeutic regimen, and in certain cases, may be a requirement in certain therapies. For example, the drug requirements of a patient may not be ascertainable prior to the commencement of a therapy (e.g., dose titration may be required to determine appropriate dosage), or a patient may require increasing doses (e.g., due to development of tolerance) or decreasing doses (e.g., as the patient gets well). In a constant drug delivery device, adjusting the rate of drug delivery can require the removal of the device from the body of a patient and/or detachment from a drug delivery system (e.g., detachment from a catheter) and adjustment or even replacement of the device.

There is thus a need in the field for a mechanism which allows for adjustment of the rate of a drug delivery device yet obviates the need for complex or bulky regulatory elements associated with the drug delivery device. The present invention addresses this problem.

SUMMARY OF THE INVENTION

The present invention features methods and devices for modulating the rate of delivery of a drug formulation from a drug delivery device by diverting drug away from a drug delivery pathway. In one embodiment, a flow regulator is positioned relative to a drug delivery pathway of a drug delivery system so that adjustment of the flow regulator can provide for diversion of drug away from the drug delivery pathway. Diverted drug can be either delivered into the systemic circulation of the subject, or can be captured in a waste reservoir.

In one aspect the invention features a flow regulator comprising a delivery conduit defining a proximal delivery inlet, a distal delivery outlet, and a delivery lumen extending between the proximal delivery inlet and the distal delivery outlet, the delivery conduit lumen defining a delivery pathway; and a diversion element positioned at the diversion inlet so as to facilitate diversion of flow of drug away from the delivery pathway.

In another embodiment, the flow regulator further comprises a diversion conduit defining a diversion inlet, a diversion outlet, and a diversion lumen extending between the diversion inlet and diversion outlet, the diversion conduit lumen defining a diversion pathway, wherein the diversion inlet is in fluid communication with the delivery conduit lumen. In this latter embodiment, drug is diverted from the delivery pathway and into the diversion pathway defined by the diversion conduit.

In another aspect the invention features a drug delivery system comprising a flow regulator and a drug delivery device, and optionally a drug delivery catheter.

In another aspect the invention features methods for administering drug to a subject and for controlling an amount of drug administered to a subject using the flow regulator of the invention.

A primary object of the invention is to provide a device and method for adjustment of the rate at which drug is delivered from a drug delivery device.

Another advantage of the invention is that the control of drug delivery from a drug delivery device to a treatment site is accomplished without the need for adjustment of any element the drug delivery device per se, e.g., without adjusting the volume rate of delivery generated by a drug delivery device. This is particularly advantageous where there may be particular difficulties or inconveniences in adjusting the amount of drug delivered from the drug delivery device.

Another important advantage of the invention is that the devices of the invention can be used in a manner that avoids the need to perform invasive procedures to adjust the dose delivered from a drug delivery device. For example, the flow regulator can be provided such that the diversion element of the flow regulator remains accessible outside the subject's body. Alternatively, the diversion element can be remotely controllable, thus allowing for adjustment of the implanted flow regulator from outside the body.

The invention is also advantageous for use where microquantities of drug are to be delivered to a treatment site, where the treatment site is a relatively confined space, and/or where the drug delivery is site-specific. In these contexts, diversion of even a small volume of drug can elicit a proportionately greater effect upon the total volume of drug delivered to the treatment site and/or the biological effect at the treatment site.

Another advantage of the invention is that where the invention is used in connection with delivery of drug to a specific treatment site. The diverted, waste drug can be dumped into the systemic circulation, where the drug is rapidly metabolized, inactivated, and/or eliminated and thus has no substantial systemic effect upon the subject. Only drug delivered to a specific treatment site has the desired biological effect. Thus the invention can be particularly attractive where the delivery of a therapeutically effective amount of drug can be accomplished through delivery at a relatively low volume rate (e.g., from about 0.01 $\mu$l/day to about 200 $\mu$l/day, usually about 0.04 $\mu$l/day to about 20 $\mu$l/day, more usually about 0.1 $\mu$l/day to about 8.0 $\mu$l/day) or in microquantities, where only a very small amount of drug need be diverted to provide for adjustment of dose delivered to a specific treatment site.

These and other objects, advantages and features of the present invention will become apparent to those skilled in the art upon reading this disclosure in combination with drawings wherein like numerals refer to like components throughout.

DETAILED DESCRIPTION OF THE PREFERRED EMBODIMENTS

Figure 1A:
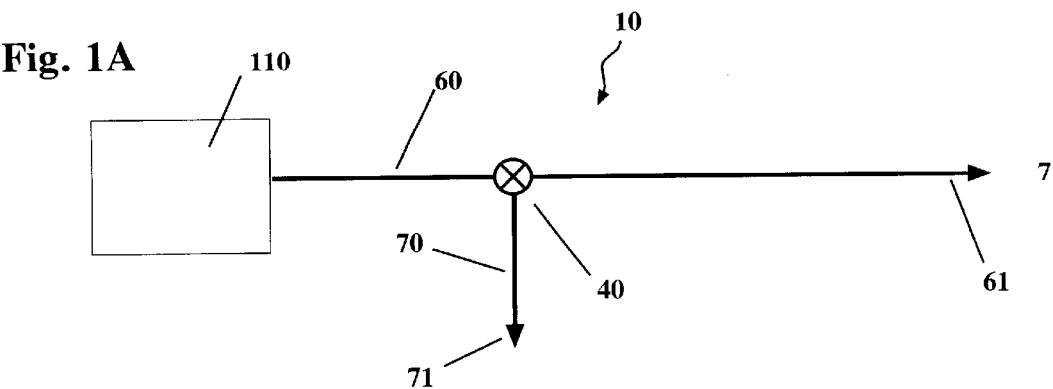
FIGS. 1A, 1B, and 1C are schematics outlining the method of drug delivery control and use of a flow regulator to accomplish same.

Before the present methods and devices are described, it is to be understood that this invention is not limited to the particular embodiments described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an," and "the" include plural referents unless the context clearly dictates otherwise. Thus, for example, reference to "a formulation" includes mixtures of different formulations, and reference to "the method of delivery" includes reference to equivalent steps and methods known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the specific methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

"Drug delivery system" is meant to refer to any device or combination of devices that can provide for transfer of drug from a drug reservoir to a treatment site. "Drug delivery device" thus encompasses, for example, a drug delivery device (e.g., implantable pump) with a flow regulator of the invention; a drug delivery device, flow regulator, and drug delivery catheter combination; and the like.

The term "treatment site" as used herein is meant to refer to a desired site for delivery of drug from a drug delivery device of the invention. "Treatment site" is thus meant to include, although is not necessarily limited to, a subcutaneous, percutaneous, intravenous, intrathecal, intramuscular, intra-arterial, intravascular, intraperitoneal, intraspinal, epidural, intracranial, peritumoral, or intratumoral (i.e., within a cancerous growth) site within a subject, as well as sites within or near a selected organ or tissue (e.g., central nervous system (e.g., intraspinal (e.g., epidural, intrathecal, etc.) within the spinal fluid, brain, etc.), peripheral nervous system, kidney, liver, pancreas, heart (e.g., intrapericardial), lung, eye, ear (e.g., inner ear), lymph nodes, breast, prostate, ovaries, testicles, thyroid, spleen, etc.), digestive system (e.g., stomach, gastrointestinal tract, etc.), skeletal muscle, bone, urinary bladder, gall bladder, adrenal gland, adipose tissue, parathyroid gland, uterus, fallopian tube, skin, into a vessel associated with the circulatory system (e.g., artery, arteriole, blood vessel, vein, capillary bed, lymph vessel, particularly arteries that feed a selected organ or tissue)), a tumorous growth (e.g., cancerous tumor (e.g., solid tumor), cyst, etc.), at a site associated with a microbial infection (e.g., bacterial, viral, parasitic or fungal infection), or to an autologous or synthetic graft (e.g., a vascular graft).

The term "access site" or "implantation site" is used to refer to a site on or in a subject at which a catheter of the invention is introduced for implantation and positioning within the subject's body, e.g., for delivery of drug to a desired treatment site. For example, where a catheter is implanted in a subject for delivery of drug to the spinal cord, the access site or implantation site can be a subcutaneous site at which a proximal end of the catheter is substantially retained, and the treatment site is a position within or adjacent the spinal cord (treatment site) at which a distal end of the catheter is positioned for delivery of drug.

The term "subject" is meant any subject, generally a mammal (e.g., human, canine, feline, equine, bovine, etc.), to which drug delivery is desired.

The terms "drug," "therapeutic agent," or "active agent" as used herein are meant to encompass any substance suitable for delivery to a treatment site of a subject, which substances can include pharmaceutically active drugs, as well as biocompatible substances that do not exhibit a pharmaceutical activity in and of themselves, but that provide for a desired effect at a treatment site, e.g., to flush or irrigate a treatment site (e.g., saline), provide for expression or production of a desired gene product (e.g., pro-drug, polynucleotide, and the like), etc. In general, "drug" and the like are used to encompass any drug administered by parenteral administration, particularly by injection (e.g., intravascularly, intramuscularly, subcutaneously, intrathecally, etc.). Drugs compatible for delivery using the devices and methods of the invention are discussed below, and are readily apparent to the ordinarily skilled artisan upon reading the disclosure provided herein. Drugs may optionally be provided in combination with pharmaceutically acceptable carriers and/or other additional compositions such as antioxidants, stabilizing agents, permeation enhancers, etc.

The term "therapeutically effective amount" is meant an amount of a drug, or a rate of delivery of a drug, effective to facilitate a desired therapeutic effect. The precise desired therapeutic effect will vary according to the condition to be treated, the drug to be administered, and a variety of other factors that are appreciated by those of ordinary skill in the art. Determinations of precise dosages are routine and well within the skill in the art.

The term "treatment" is used here to cover any treatment of any disease or condition in a mammal, particularly a human, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the disease and/or its symptoms.

Overview

Figure 1B:
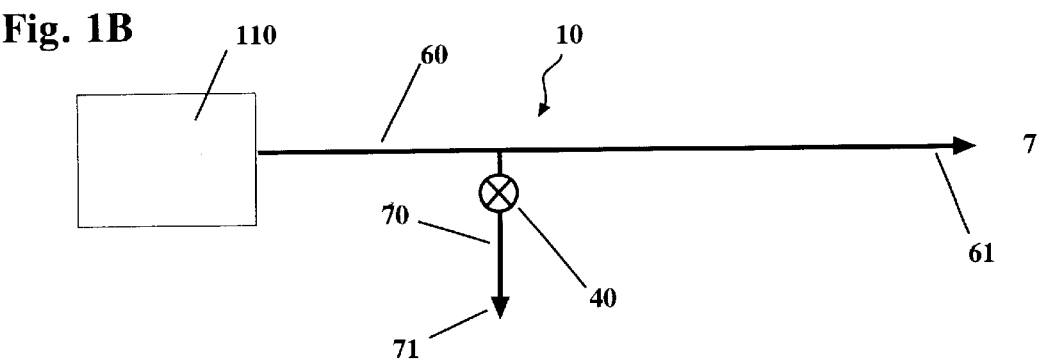
Figure 1C:
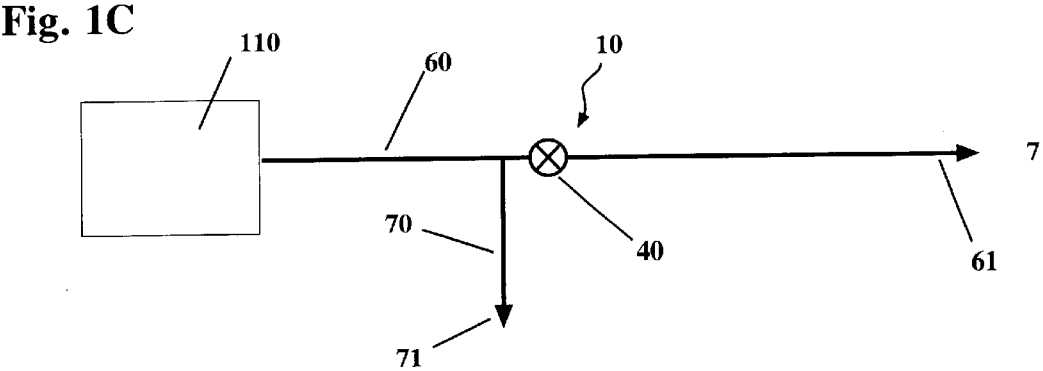

The present invention encompasses methods and devices for regulating the rate of drug delivery from a drug delivery device. As illustrated in the schematic of FIGS. 1A–1C, the invention accomplishes regulation of drug delivery rate from a drug delivery device 110 by diverting the flow of drug away from a primary drug delivery pathway 60 (flow direction indicated by arrow 61) and into diversion pathway 70 (flow direction exemplified by arrow 71). Diversion of drug away from the drug delivery pathway 60 is accomplished using a flow regulator 10. In general, flow regulator 10 comprises: 1) a delivery conduit, which defines delivery pathway 60 that flows toward a treatment site during use; and 2) a diversion element 40 (represented schematically by a valve symbol), which may be a valve or other element that facilitates diversion of drug flow from the delivery pathway 60, e.g., out of the delivery conduit through a proximal drug exit outlet positioned along the delivery conduit body. In another embodiment, the flow regulator comprises a diversion conduit, which is in fluid communication with the delivery conduit and defines diversion pathway 70 that flows away from delivery pathway 60. For clarity, the majority of embodiments of the invention exemplified herein comprise both a delivery conduit and a diversion conduit; however, the invention is not meant to be so limited.

The flow regulator can be provided in a variety of embodiments. For example, the diversion element of the flow regulator can be positioned at the juncture of the delivery and diversion pathways (see, e.g., FIG. 1A), at a site of the delivery pathway distal to the diversion outlet (see, e.g., FIG. 1B), or, where the flow regulator comprises a diversion conduit that defines the diversion pathway, the diversion element can be positioned along the body of the diversion conduit (see, e.g., FIG. 1C).

In one embodiment, the diverted drug is collected in a waste reservoir. This embodiment is particularly useful where the drug delivery system is for systemic drug delivery, i.e., the rate of systemic drug delivery can be regulated by diverting the drug into a waste reservoir.

In another embodiment, drug diverted into the diversion pathway 70 can be delivered to a site within the subject where the drug will have few or no undesirable side effects, e.g., to a site in the body away from the site of action of a drug. This embodiment of the invention is particularly useful where there is a local advantage to delivery of drug to a target site, which local advantage can be due to, for example, delivery of drug to directly to the desired site of action (e.g., to avoid side effects associated with systemic delivery), concentration effects (e.g., site-specific delivery provides for a drug concentration at the treatment site that is difficult or undesirable to accomplish through systemic delivery routes), and/or characteristics of the drug itself (e.g., short half-life, inactivation in the systemic circulation, etc.). This embodiment of the invention provides an elegant means for regulating drug delivery rate by taking advantage of the difference in the amount of drug that elicits a biological effect at a specific site relative to an amount of drug that elicits a biological effect when delivered systemically. The invention takes advantage of this difference in relative therapeutic thresholds to use the systemic circulation as a "waste reservoir" for drug diverted from a drug delivery pathway that targets a specific treatment site.

Specific exemplary embodiments of the invention are described below in more detail. The embodiments described below and in the figures are only exemplary and are not meant to be limiting in any way.

Exemplary Flow Regulator Embodiments

The flow regulator of the invention can comprise any element suitable for facilitating a degree of opening and closing of the drug diversion pathway and/or for redirecting a portion of the drug flow in delivery pathway into the diversion pathway. Diversion elements suitable for use in a flow regulator of the invention include, but are not necessarily limited to, any of a variety of remotely controllable or manually actuated valves, piezoelectric valves, solenoids, and switches, as well as any of a variety of devices that can provide for varying relative resistance to flow through the drug delivery pathway and the drug diversion pathway of the drug delivery system.

Figure 1D:
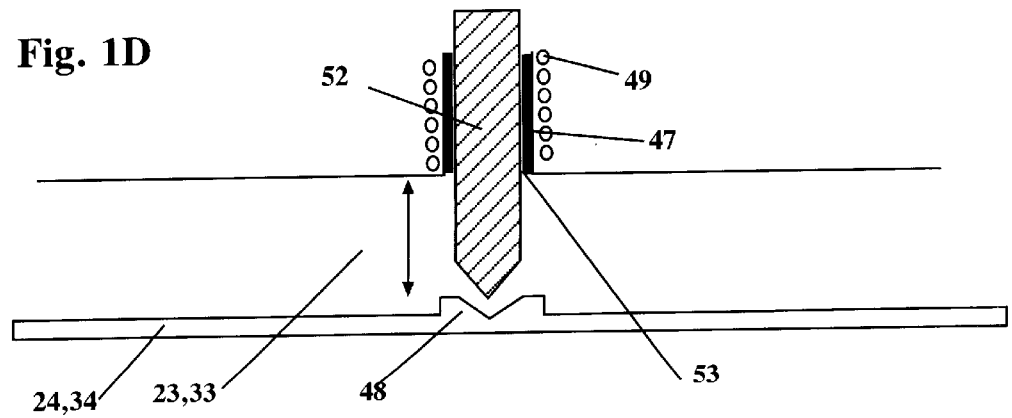
FIG. 1D is a cut-away view of a solenoid useful as a diversion element in the flow regulator of the invention.

For example, in one embodiment, the diversion element 40 is a valve, which, as exemplified in FIG. 1D, can be in the form of a solenoid 47. Any of a variety of solenoids, which are well known in the art, are suitable for use as valves in the diversion element. For example, the diversion element can be a valve in the form of a solenoid. The solenoid can be positioned for opening and closing of a proximal drug exit outlet of a delivery conduit, for opening and closing of the delivery conduit lumen (e.g., thereby increasing flow through a proximal drug exit outlet of a delivery conduit), or within a diversion conduit.

Various solenoids suitable for use in the invention are well known in the art. As exemplified in FIG. 1D solenoid 47 can comprise a rod or piston 52 which is slidably received within shaft 53. Seals 47 provide a fluid-tight seal to inhibit backflow into the solenoid mechanism. FIG. 1D depicts the solenoid positioned for opening and closing of a conduit lumen, e.g., positioned within the body 24, 34 of a delivery conduit 20 or of a diversion conduit 30 to facilitate varying degrees of opening and closing of the delivery conduit lumen 24 or diversion conduit lumen 34. When the solenoid 47 is in the open position, rod 52 is completely or partially withdrawn into shaft 53 to allow flow through lumen 24, 34. When the solenoid 47 is in the fully closed position, rod 52 is received within abutment 48, providing a fluid seal between rod 52 distal end 51 and the abutment 48. Supplying power to electrical coils 49 surrounding rod 52 causes movement of rod 52 within shaft 53 to facilitate varying degrees of opening and closing of the lumen or other opening.

Figure 2:
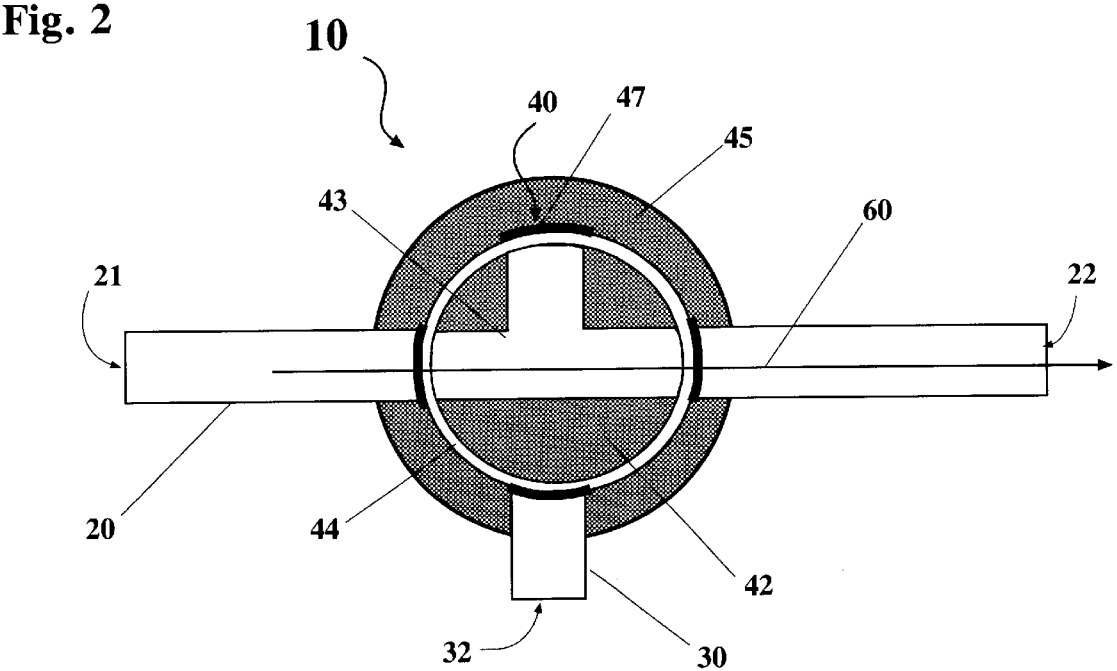
FIG. 2 is a cut-away view of a flow regulator 10 comprising a rotatable valve 42 with the delivery conduit 20 open.
Figure 3:
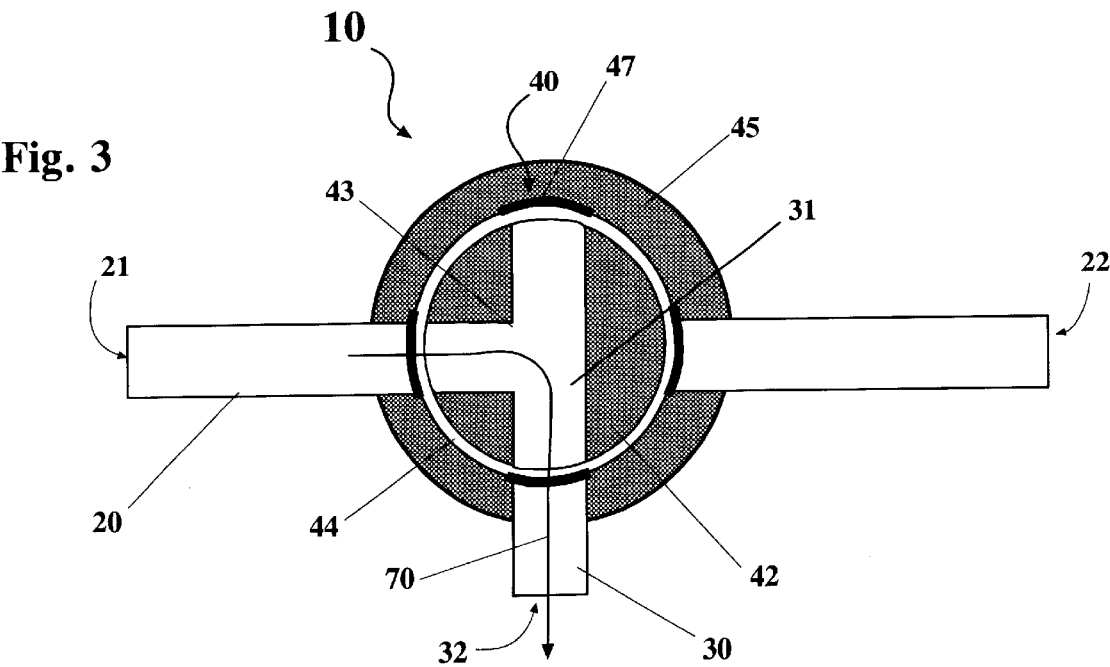
FIG. 3 is a cut-away view of a flow regulator 10 comprising a rotatable valve 42 with the diversion conduit 30 open.

In another embodiment, illustrated in FIGS. 2 and 3, flow regulator 10 comprises a diversion element in the form of rotatable valve 42 comprising a substantially T-shaped conduit 43 seated within a ring-like structure 44. The rotatable valve is positioned in a drug delivery conduit 20 and a drug diversion conduit 30. Drug delivery conduit 20 comprises a substantially elongate member defining a lumen through which drug delivery pathway 60 travels from a proximal drug inlet opening 21 to a distal drug delivery outlet opening 22 when the valve 42 is in a position as illustrated in FIG. 2. Drug diversion conduit 30 comprises a substantially elongate member defining a diversion inlet 31 and a diversion outlet 32, and further defining a lumen through which a drug diversion pathway 70 travels when the valve 42 is in a position as illustrated in FIG. 3. Delivery conduit 20 and diversion conduit 30 can be provided as separate, attached components, or molded as a single piece (e.g., the diversion conduit can be an extended orifice from a side wall of the delivery conduit). The valve 42 and at least portions of drug delivery conduit 20 and diversion conduit 30 are mounted within a housing element 45 to maintain the lumen of conduits 20, 30, and 43 within substantially the same plane and to optionally provide a liquid tight or liquid resistant compartment for the flow regulator 40, e.g., to prevent flow of environmental fluid into the openings of the valve conduit 43. Housing element 45 may comprise elements to facilitate positioning of flow regulator valve 40 and/or to ensure that rotation of valve 40 is stopped at a position that provides for fluid communication between drug inlet opening 21, through valve 40 and out either distal outlet 22 (FIG. 2) or diversion outlet 32 (FIG. 3). Seals 47 positioned around the outer circumference of rotating valve 40 and/or at the openings of the drug delivery conduit 20, drug diversion conduit 30, and at a position within housing element 45 to ensure closure of an end of T-shaped conduit 43 that is not in communication with either delivery conduit 20 or diversion conduit 30 during use (see, e.g., FIGS. 2 and 3) provide for a liquid-tight seal to facilitate flow through the valve conduits. The rotatable valve 42 of the flow regulator can be manually or remotely actuated, and can be rotated using mechanical, electromechanical (e.g., a microdrive engine), or electromagnetic (e.g., a solenoid) means.

Figure 4:
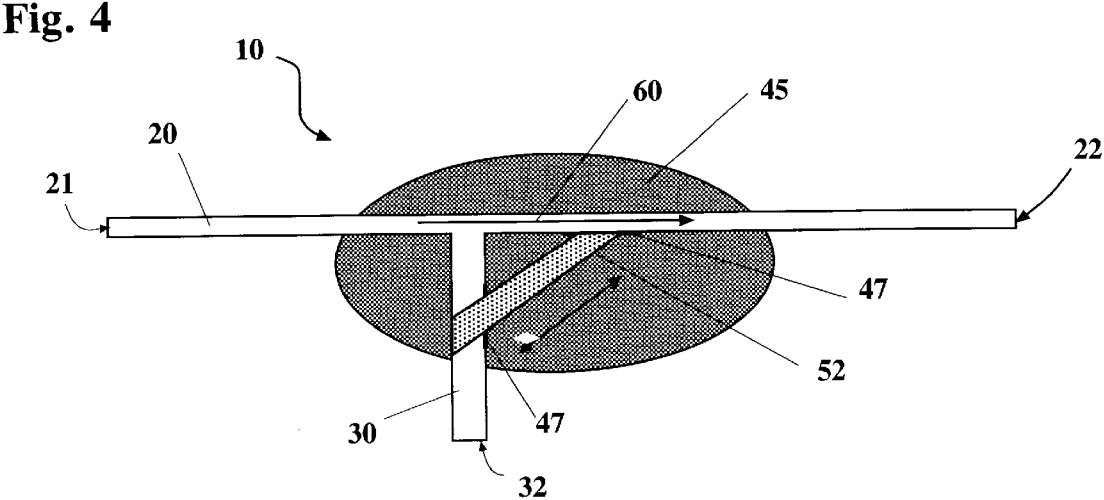
FIG. 4 is a cut-away view of a flow regulator 10 comprising a rod element 52 positioned so that the delivery conduit 20 is open and the diversion conduit 30 is closed.
Figure 5:
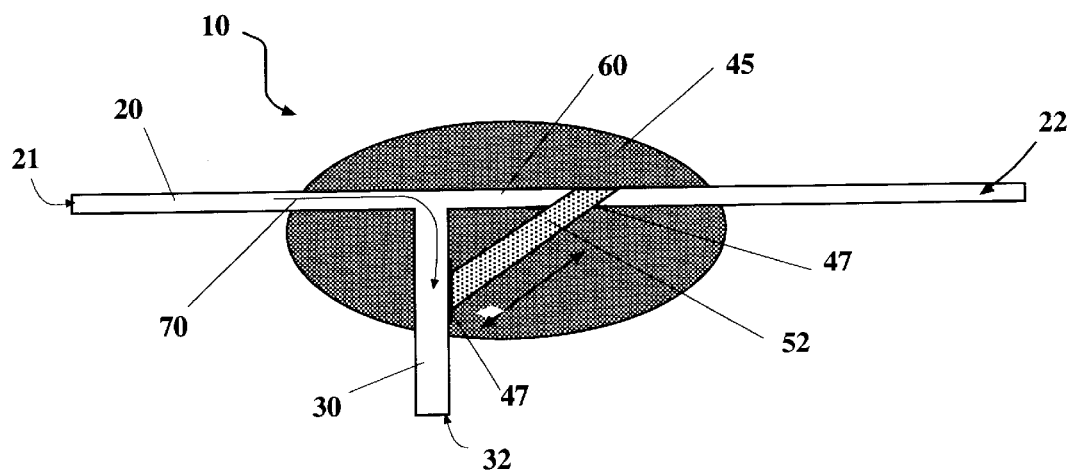
FIG. 5 is a cut-away view of a flow regulator 10 comprising a rod element 52 positioned so that the delivery conduit 20 is closed and the diversion conduit 30 is open.

In another embodiment, the flow regulator 10 comprises diversion element in the form of a slidable rod element 52 in a gearshift-type valve mechanism (see, e.g., FIGS. 4 and 5). The ends of the rod 52 are slidably received within side openings of the diversion conduit 30 and of the drug delivery conduit 20. Seals 47 at each of these openings provide a liquid-tight seal with rod 52. FIG. 4 shows rod 52 positioned such that drug delivery conduit 20 is completely open and diversion conduit 30 is completely closed, e.g., all drug formulation introduced at inlet 21 flows through drug delivery pathway 60 to drug outlet 22. Sliding of rod 52 into the lumen of drug delivery conduit 20 can providing for varying and inversely proportional degrees of closing of drug delivery conduit 20 and opening of diversion conduit 30, up to and including complete closure of drug delivery conduit 20 and complete opening of diversion conduit 30 such that substantially all drug introduced into inlet 20 flows through diversion pathway 70. The flow regulator can be housed within a housing element 45 to protect the mechanics of the flow regulator from environmental fluids. Movement of rod 52 can be accomplished manually or remotely actuated, and can be rotated using mechanical, electromechanical (e.g., a microdrive engine), or electromagnetic (e.g., a solenoid) means.

Figure 6:
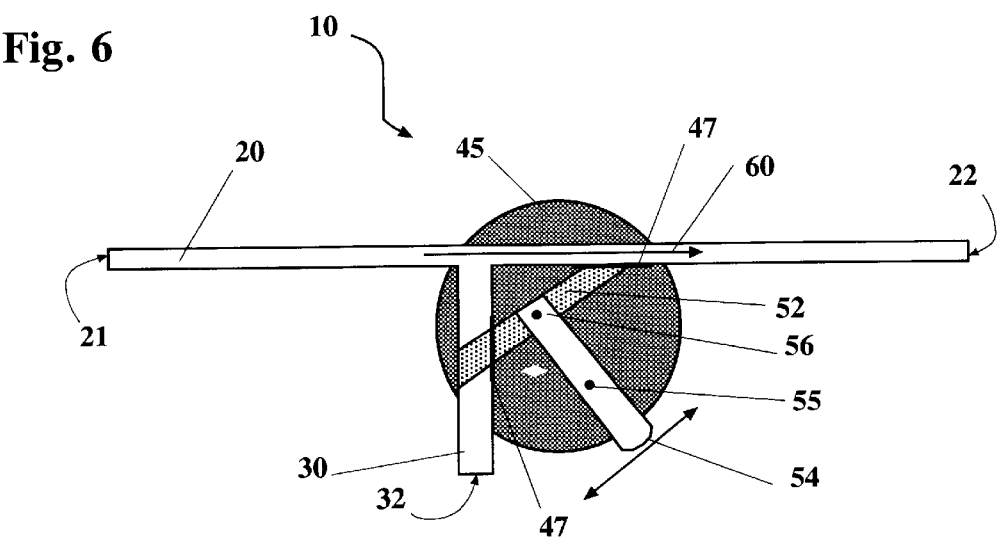
FIG. 6 is a cut-away view of a flow regulator 10 comprising a rod 52 and toggle switch 54 positioned so that delivery conduit 20 is open and diversion conduit 30 is closed.
Figure 7:
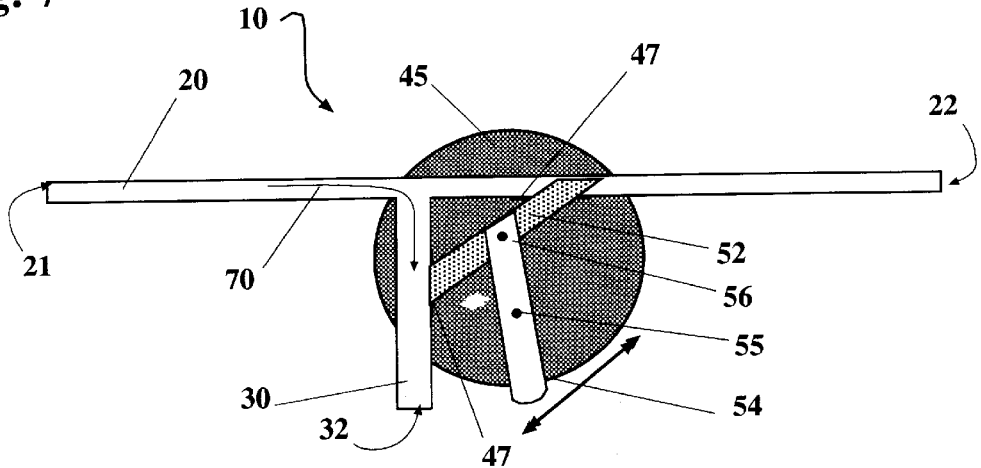
FIG. 7 is a cut-away view of a flow regulator 10 comprising a rod 52 and toggle switch 54 positioned so that delivery conduit 20 is closed and the diversion conduit 30 is open.

In another embodiment, flow regulator 10 comprises a diversion element comprising a rod element 52 and a toggle switch 54 contained within housing element 45 (FIGS. 6 and 7). As in the exemplary embodiments illustrated in FIGS. 4 and 5, rod 52 is slidably received within a side opening of the diversion conduit 30 and a side opening of the drug delivery conduit 20, with seals 47 at each of these openings providing a liquid-tight seal with rod 52. Toggle switch 54 is attached to rod 52, and hinged within housing element 45 at pivot point 55 and rod 52 at pivot point 56. Movement of toggle switch 54 in a direction toward delivery conduit 20 results in simultaneous opening of delivery conduit 20 and closing of diversion conduit 30; movement of toggle switch 54 in a direction toward the diversion conduit 30 results in simultaneous closing of delivery conduit 20 and opening of diversion conduit 30. The toggle switch 54 and rod 52 can be adjusted to provide for any relative degree of opening and closing of the conduits 20 and 30. Movement of toggle switch 55 and rod 52 can be accomplished manually or remotely actuated, and can be rotated using mechanical, electromechanical (e.g., a gear drive engine), or electromagnetic (e.g., a solenoid) means.

Figure 8:
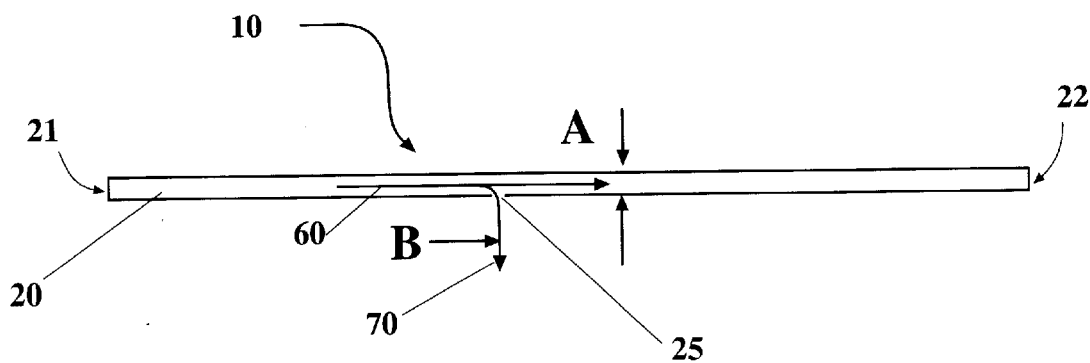
FIG. 8 is schematic illustrating regulation of flow rate of a delivery pathway 60 by modulation of relative resistance upon delivery pathway 60 and diversion pathway 70.

In another embodiment, flow diversion is accomplished by deformation of the diversion conduit 30 and/or delivery conduit 20 to vary their relative inner diameters. As illustrated schematically in FIG. 8, increasing the resistance on delivery path 60 (e.g., at point A) relative to the resistance on diversion pathway 70 (e.g., at point B) will result in diversion of drug into diversion pathway 70, e.g., out a proximal drug exit outlet 25 which may be in fluid communication with a diversion conduit 30 (represented by dashed lines in FIG. 8). Likewise, increasing the resistance on diversion path 70 relative to the resistance on delivery pathway 60 will result in less drug flowing through diversion pathway 70 and more flowing through delivery pathway 60. Resistance at diversion pathway 70 and/or delivery pathway 60 can be provided by application of external pressure which can be provided by mechanical force, hydraulic pressure and the like to impinge against a deformable conduit wall portion and/or to pinch the conduit closed.

A starting delivery conduit flow rate greater than a diversion conduit flow rate can be established in order to prevent drug from simply flowing through the diversion pathway with little or no drug reaching delivery outlet at the delivery conduit distal end. For example, the delivery conduit inner diameter can be greater than the diversion conduit inner diameter, thus providing for a slower flow rate through the diversion conduit. Alternatively or in addition, the proximal drug exit outlet of the delivery conduit can be of a small diameter which allows only a "slow drip" through the proximal drug exit outlet unless flow resistance is increased in the delivery conduit at a site distal to the drug exit outlet. Alternatively or in addition, the diversion conduit inner diameter can be of a smaller diameter relative to the delivery conduit inner diameter, allowing only a slow drip into the diversion conduit in the absence of external pressure on the delivery conduit. Alternatively or in addition, the proximal drug exit outlet and/or diversion conduit can be completely or partially filled with a porous or semi-porous material to increase flow resistance in the diversion conduit relative to the delivery conduit.

Figure 9:
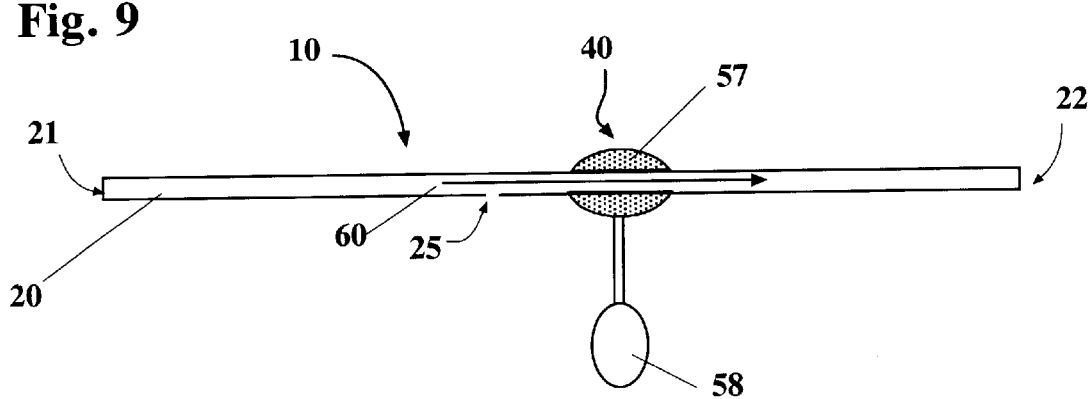
FIG. 9 is a cut-away view of flow regulator 10 comprising an substantially uninflated cuff 57 positioned over a deformable distal portion of delivery conduit 20.
Figure 10:
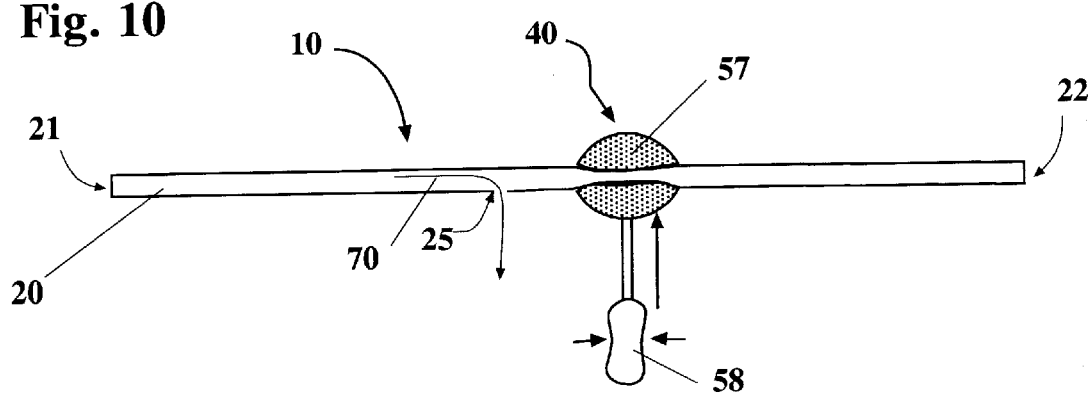
FIG. 10 is a cut-away view of flow regulator 10 comprising an inflated cuff 57 positioned over a deformable distal portion of delivery conduit 20 to impede flow through delivery pathway 60 and increase flow through diversion pathway 70.

Modulating the relative flow resistance of the delivery pathway 60 relative to the diversion pathway 70 can be accomplished in a variety of ways. For example, the diversion element of the flow regulator can comprise a compression element that provides a means for alternately decreasing and increasing the inner diameter of the delivery conduit, of the diversion conduit, or both. In one embodiment exemplified in FIGS. 9 and 10, flow regulator 10 comprises a diversion element in the form of a compression element, where the compression element is an inflatable cuff 57 positioned over a deformable distal portion of delivery conduit 20. Cuff 57 can be inflated using a balloon-like inflating element 58, which comprises a balloon, a connector that communicates the balloon with the cuff, and a one-way valve positioned between the balloon and the cuff. When substantially uninflated, cuff 57 does not cause any substantial deformation of delivery conduit 20. Depression of the balloon 58 results in inflation of cuff 57, which in turn results in deformation of delivery conduit 20 beneath cuff 57 and restriction of flow of drug through delivery pathway 60, thus increasing flow through diversion pathway 70.

Figure 11:
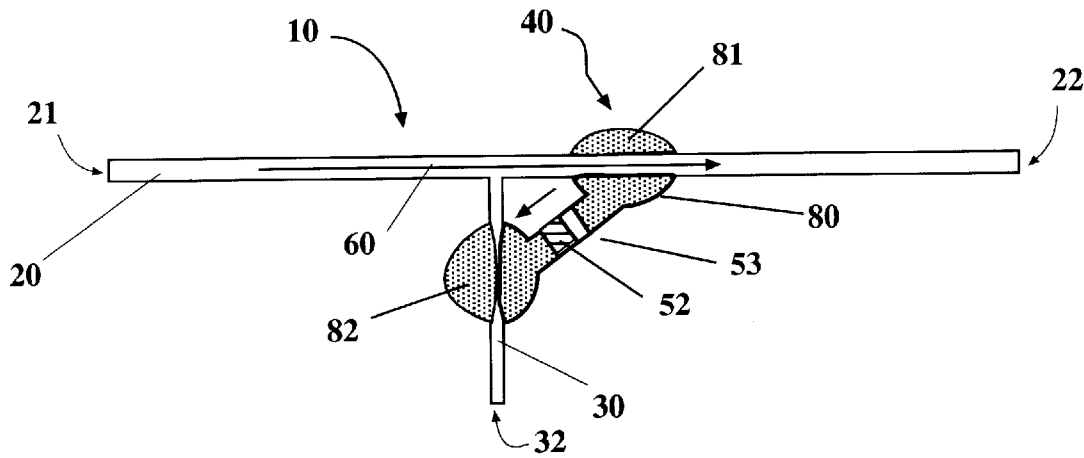
FIGS. 11 and 12 are cut-away views of flow regulator 10 comprising a hydraulic cuff 57 positioned over a deformable distal portion of delivery conduit 20 and over a deformable portion of diversion conduit 30.
Figure 12:
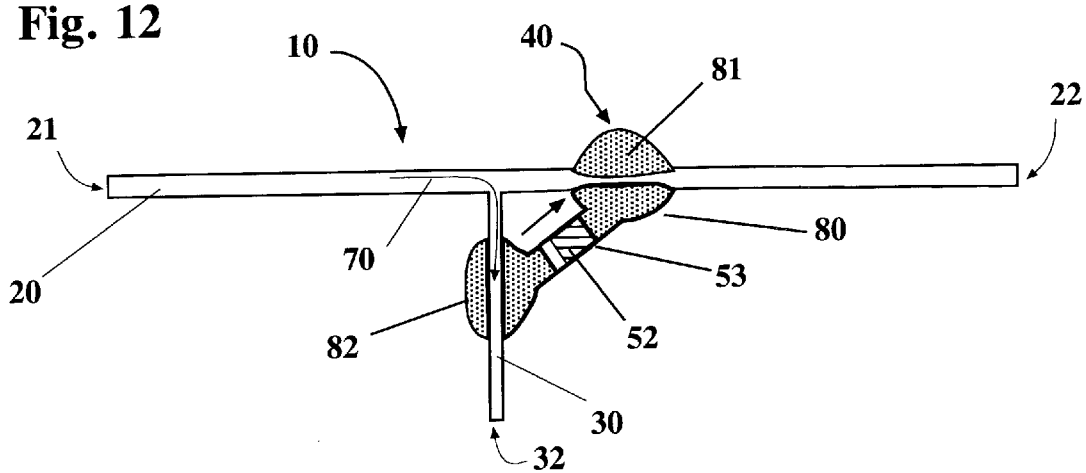

In another embodiment, the relative flow resistance in delivery conduit 20 and diversion conduit 30 is controlled using a hydraulic cuff 80, which comprises balloon elements 81 and 82 positioned over a deformable distal portion of delivery conduit 20 and over a deformable portion of diversion conduit 30, respectively. The hydraulic cuff 80 comprises a rod 52 that is slidably positioned within shaft 53. Movement of rod 52 within shaft 53 in a direction toward diversion conduit 30 increases pressure on gas or fluid in balloon element 82, and a concomitant decrease in pressure on gas or fluid in balloon element 81, resulting in relatively increased flow through delivery conduit 20 and relatively decreased flow through diversion conduit 30 (FIG. 11). Movement of rod 52 within shaft 53 in a direction toward delivery conduit 20 increases pressure on gas or fluid in balloon element 81, and a concomitant decrease in pressure on gas or fluid in balloon element 82, resulting in relatively increased flow through diversion conduit 30 and relatively decreased flow through delivery conduit 20 (FIG. 12).

Figure 13:
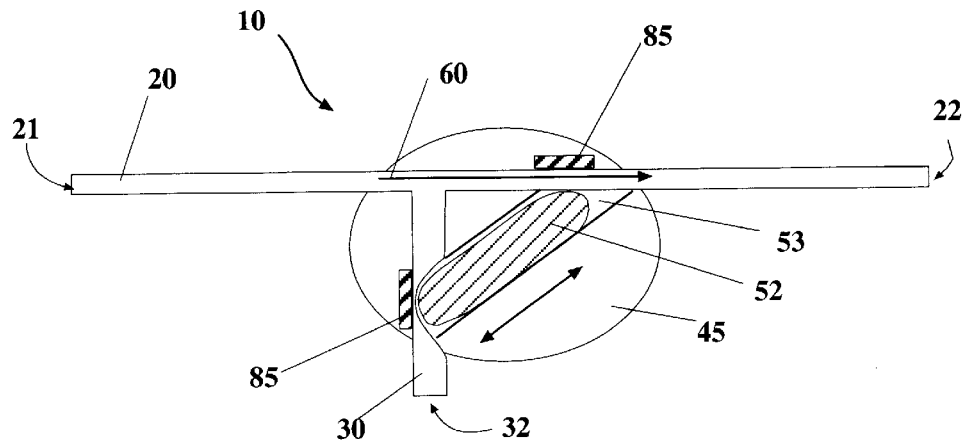
FIG. 13 is a cut-away view of flow regulator 10 comprising a rod 52 positioned for impinging upon deformable surfaces of delivery conduit 20 and diversion conduit 30, with rod 52 in position for substantial closing of diversion conduit 30.
Figure 14:
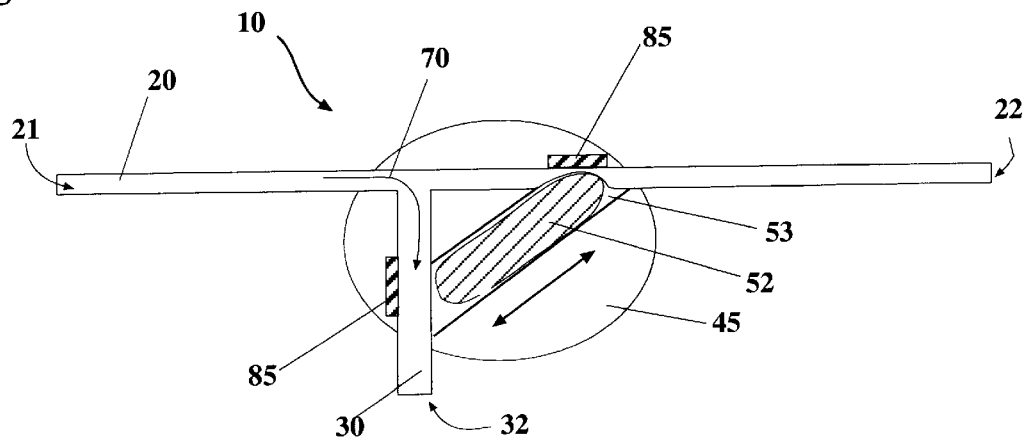
FIG. 14 is a cut-away view of flow regulator 10 comprising a rod 52 positioned for impinging upon deformable surfaces of delivery conduit 20 and diversion conduit 30, with rod 52 in position for substantial closing of delivery conduit 20.

In another embodiment exemplified in FIGS. 13 and 14, the diversion element of flow regulator 10 is a compression element comprising a rod element 52 slidably positioned within shaft 53 so as to be in alternate or simultaneous contact with a deformable portion of diversion conduit 30 and a deformable portion of delivery conduit 20 distal to the diversion conduit 30. Flow regulator 10 is contained with housing 45, which housing can provide for a fluid-resistant seal to inhibit entry of environmental fluids into the flow regulator mechanism. Abutment walls 85 are positioned adjacent delivery conduit 20 and diversion conduit 20 at a wall opposite the deformable wall to be contacted by rod 52. Abutment walls 85 provide resistance to the pressure generated by rod 52 when impinging upon the opposite conduit wall to deform the conduit and modulate the conduit inner diameter, e.g., to facilitate deformation of the conduit wall in contact with rod 52 rather than movement of the entire conduit. Movement of rod 52 within shaft 53 in a direction toward diversion conduit 30 results in deformation of a deformable portion of diversion conduit 30, resulting in complete or partial pinching of the deformable portion of diversion conduit 30 (see, e.g., FIG. 13) with simultaneous opening of delivery conduit 20. Movement of rod 52 in a direction toward delivery conduit 20 results in deformation of a deformable portion of delivery conduit 20, resulting in complete or partial pinching of the deformable portion of delivery conduit 20 with simultaneous opening of diversion conduit 30 (see, e.g., FIG. 14). Rod 52 can be positioned to provide any of a variety of gradations of relative opening and closing of delivery conduit 20 and diversion conduit 30. Movement of rod 52 can be accomplished manually or remotely actuated, and can be rotated using mechanical, electromechanical (e.g., a microdrive engine), or electromagnetic (e.g., a solenoid) means. In a similar embodiment, rod 52 is provided in association with a toggle switch that facilitates movement of rod 52, similar to the embodiment described above and in FIGS. 6 and 7.

Conduit Configuration

Figure 15:
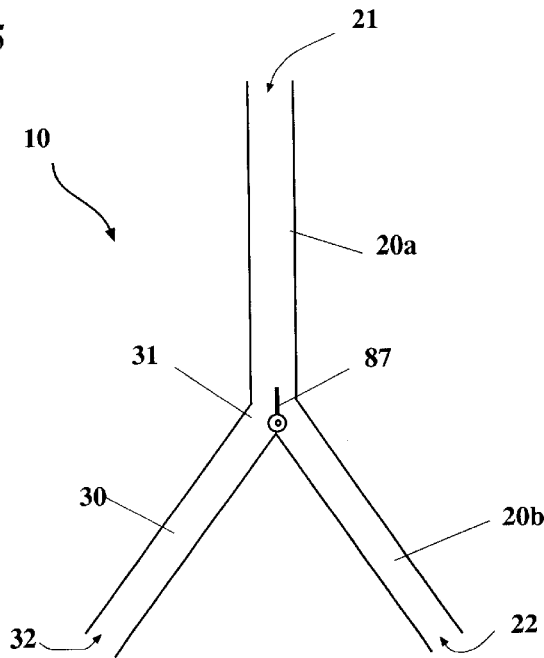
FIG. 15 is a cut-away view of a flow regulator 10 in a Y-shaped configuration, with valve 31 positioned for diversion of approximately 50% of drug into diversion conduit 30.
Figure 16:
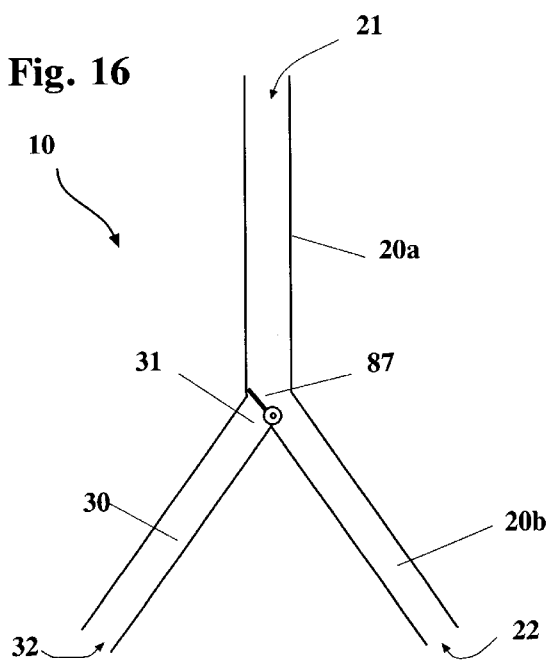
FIG. 16 is a cut-away view of a flow regulator 10 in a Y-shaped configuration, with valve 31 positioned for substantial closure of diversion conduit 30.
Figure 17:
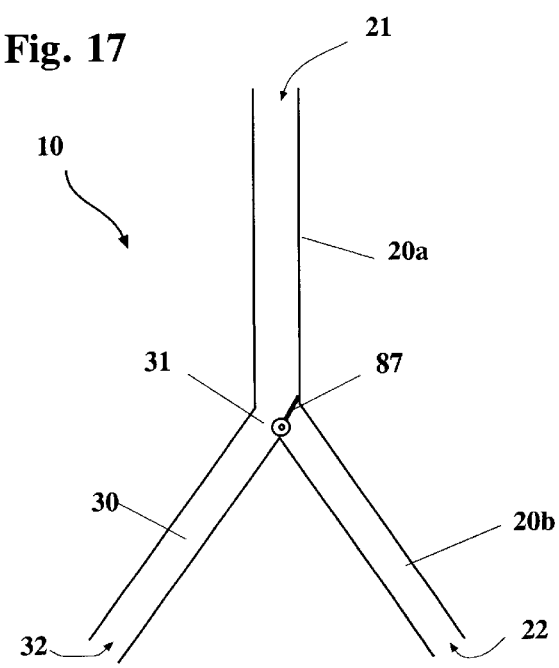
FIG. 17 is a cut-away view of a flow regulator 10 in a Y-shaped configuration, with valve 31 positioned for substantial closure of delivery conduit 20.

While the above exemplary embodiments have illustrated the flow regulators comprising both a delivery conduit and diversion conduit as comprising a T-shaped intersection between a delivery conduit and a diversion conduit, other embodiments are contemplated by the invention. As exemplified in FIGS. 15–17, a proximal portion of delivery conduit 20a extends from a drug inlet 21 to a Y-shaped branch point at which the conduit diverges to provide a diversion conduit 30 and a distal portion of the delivery conduit 20b. Flow regulator 10 comprises a flap valve 87 positioned at the conduit branch point, which flap valve 87 pivots at a point within the conduit branch point to provide for relative opening and closing of delivery conduit 20b and diversion conduit 30. FIG. 15 illustrates positioning of flap valve 87 so as to divert approximately half of the flow of drug from drug inlet 21 into delivery conduit 20b and half into diversion conduit 30. FIGS. 16 and 17 illustrate flap valve 87 positioned for substantially complete closure of diversion conduit 30 (FIG. 16) and substantially complete closure of delivery conduit 20b (FIG. 17).

Figure 18:
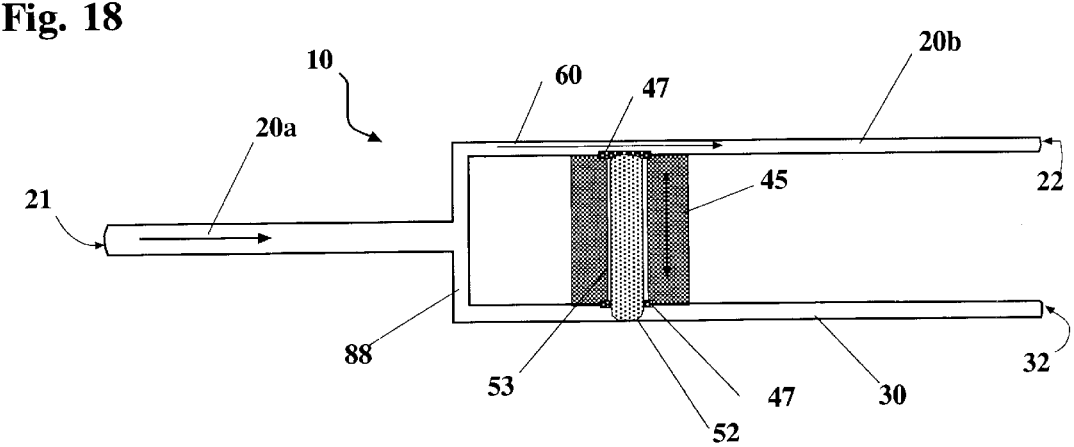
FIG. 18 is a cut-away view of a flow regulator 10 in a U-shaped configuration, with rod-like valve 57 positioned for substantially complete closure of diversion conduit 30 and substantially complete opening of delivery conduit 20.
Figure 19:
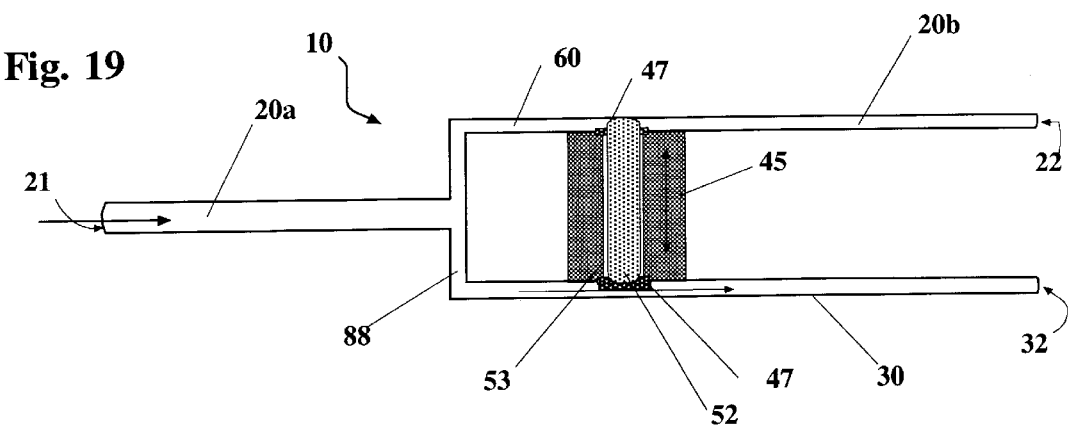
FIG. 19 is a cut-away view of a flow regulator 10 in a U-shaped configuration, with rod-like valve 57 positioned for substantially complete closure of delivery conduit 20 and complete opening of diversion conduit 30.

In another embodiment, flow regulator 10 comprises a tuning-fork or U-shaped configuration (see, e.g., FIGS. 18 and 19). In this embodiment a proximal portion of delivery conduit 20a and intersects at a connector conduit 88 which in turn is in communication with a distal delivery conduit portion 20b and with diversion conduit 30. A rod 52 is slidably received within shaft 53 and within openings in distal delivery conduit 20 and diversion conduit 30. Seals 47 positioned around the conduit openings provide for a liquid tight or liquid resistant seal to prevent leaking of drug from the conduits. Sliding of rod 52 toward diversion conduit 30 results in closing of diversion conduit 30 and simultaneous opening of distal delivery conduit 20 to allow flow through delivery pathway 60. Sliding of rod 52 toward distal delivery conduit 20b results in closing of distal delivery conduit 20b and simultaneous opening of diversion conduit 30 to allow flow of drug through diversion pathway 70. Rod 52 can be moved through mechanical, electromechanical, or electromagnetic means, and can be activated manually or remotely. For example, rod 52 can be a solenoid or a piston-like element.

Waste Reservoir Embodiments

In all embodiments described herein and contemplated by the invention, drug that flows through the proximal drug exit outlet of the delivery conduit can be optionally collected in a waste reservoir. Embodiments with waste reservoirs are particulary useful when the flow regulator is used as part of a drug delivery system wherein drug is administered systemically instead of locally. In general, the waste reservoir is a bag, pouch, container, receptacle, bellows (e.g., metal bellows) or other receiving element in fluid communication with the diversion conduit outlet and/or delivery conduit proximal drug exit outlet. The waste reservoir can be provided as an extension of the catheter body, or can be provided as a separate component that is either removably or permanently attached. Where the waste reservoir is to be positioned within the subject's body during use, it is preferably permanently attached and comprises an implantable, biocompatible material.

The waste reservoir can be of any size or shape suitable for use with the delivery exit catheter with which it is to be used. For example, the waste reservoir can be provided as a separate, closed lumen within the wall of the diversion conduit, the delivery conduit, or within a wall of a catheter used in connection with the flow regulator. Alternatively, the waste reservoir can be provided within a housing element of the flow regulator or within a chamber of a drug delivery device used in connection with the flow regulator of the invention. The waste reservoir can comprise any suitable, substantially drug-impermeable material (e.g., multilaminate impermeable polymers/metalized polymer or metal/plastic laminate), and preferably does not react in an unintended manner with the active agent formulation. The waste reservoir can be designed to facilitate removal of drug it contains, e.g., by means of a self-sealing septum that allows needle access.

In one embodiment of particular interest, the waste reservoir is provided as part of the delivery pump such that on removal of the pump from the drug delivery system (e.g., detachment of the pump from a drug delivery catheter) the reservoir is automatically removed. The waste reservoir can also be co-located with the pump or molded within the pump body.

Figure 20:
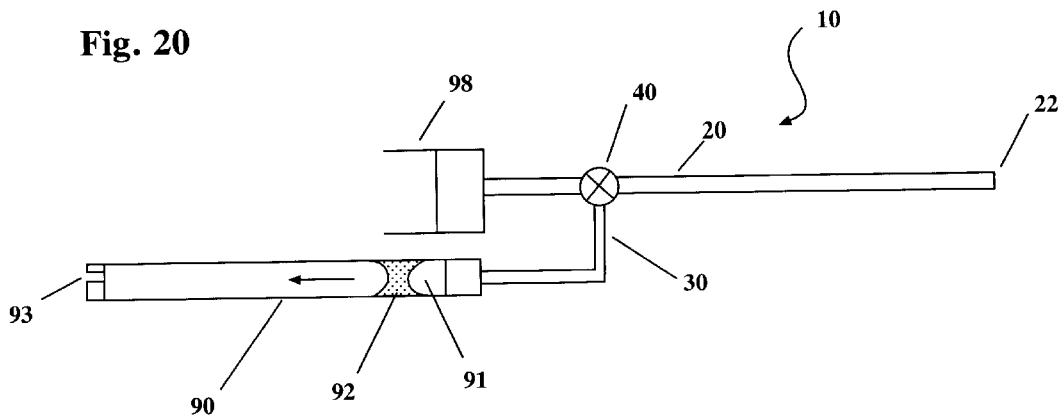
FIG. 20 is cut-away view of a flow regulator 10 of the invention comprising a waste reservoir 90.
Figure 21:
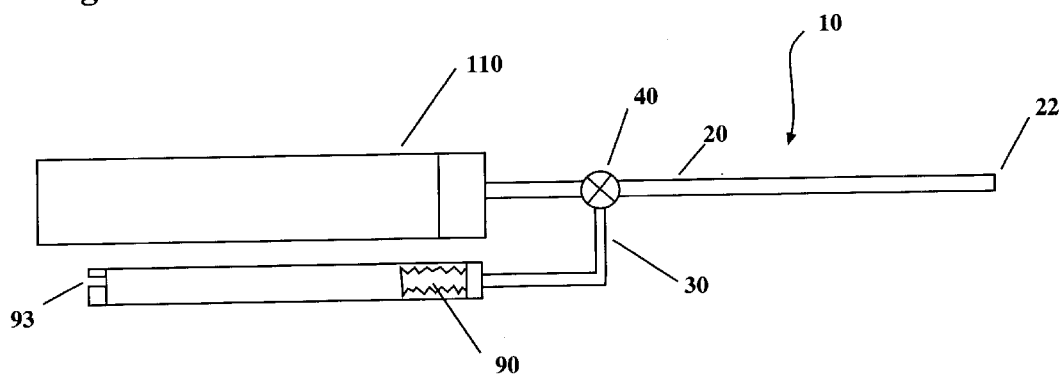
FIG. 21 is a cut-away view of a flow regulator 10 of the invention operably attached to a drug delivery device 110 and to a waste reservoir 90.

In one embodiment, exemplified in FIG. 20, the waste reservoir 90 is provided as a component of flow regulator 10. The proximal end of the delivery conduit can be adapted for receiving a drug delivery device, exemplified in FIG. 20 as device receiving chamber 98. The waste reservoir 90 of FIG. 20 comprises a waster receiving chamber 91. As wasted is delivered into waste receiving chamber 91, piston 92 is advanced in a direction toward vent hole 93, which allows for displacement of fluid or gas contained within the proximal portion of waste reservoir 90. Where the waste reservoir is provided as a detachable component, the waste reservoir can be removed when descried, e.g., when the waste reservoir is full such that piston 92 has reached the waste reservoir proximal end. In another embodiment, exemplified in FIG. 21, waste is received within an expandable bellows 94.

Flow Regulator as Element of Drug Delivery System

Figure 22:
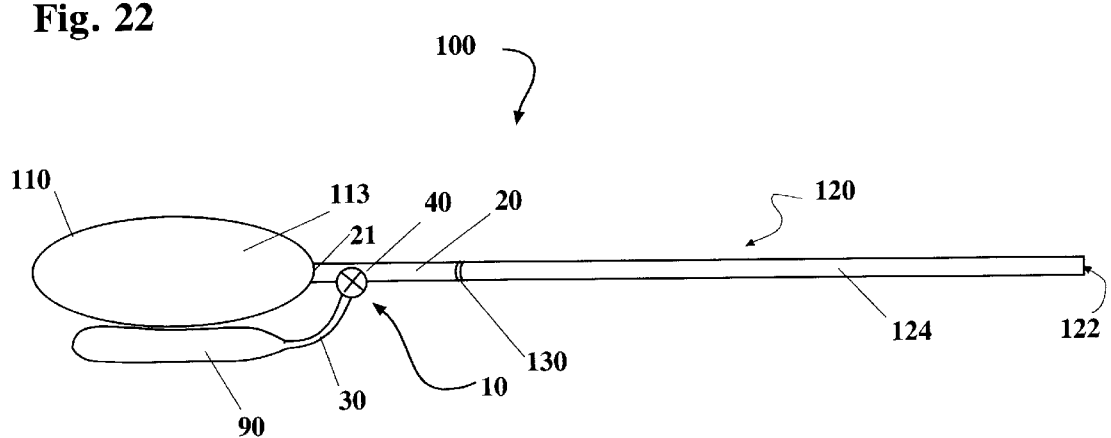
FIG. 22 is a cut-away view of a delivery system 100 of the invention comprising a drug delivery device 110 and a flow regulator 10.

The flow regulator of the invention can be provided as an integral or detachable element of a drug delivery system component. For example, the flow regulator and optional waste reservoir can be an integral or detachable portion of a drug delivery device. For example, FIG. 22 illustrates a drug delivery system 100 comprising a drug delivery device 110 and a flow regulator 40, which drug delivery system 100 can further comprise a drug delivery catheter 120. In this embodiment, flow regulator 10 is permanently attached to (e.g., via welding, adhesive bonding, etc.) or an integral component of drug delivery device 110.

The drug delivery device minimally comprises a drug release device (e.g.,a constant rate drug delivery device, such as an osmotic pump) having a proximal end and a distal end, which distal end defines a drug delivery orifice. The distal end of the drug delivery device is attached to a proximal end of the catheter so that the drug flow pathway from the drug delivery device reservoir continues through the drug delivery device orifice and into the delivery conduit of the flow regulator. The present invention finds particular use with those drug release devices that provide for delivery of drug at a pre-selected rate that cannot be readily adjusted, but can be used with any of a wide variety of drug delivery devices including, but not limited to, diffusion-based delivery system (e.g., erosion-based delivery systems (e.g., polymer-impregnated with drug placed within a drug-impermeable reservoir in communication with the drug delivery conduit of the catheter of the invention), electrodiffusion systems, and the like) and convective drug delivery systems (e.g., systems based upon electroosmosis, vapor pressure pumps, electrolytic pumps, effervescent pumps, piezoelectric pumps, osmotic pumps, etc.). Drug release devices based upon a mechanical or electromechanical infusion pump, may also be suitable for use with the present invention. Examples of such devices include those described in, for example, U.S. Pat. Nos. 4,692,147; 4,360,019; 4,487,603; 4,360,019; 4,725,852, and the like. In general, the present invention can be used in conjunction with refillable, non-exchangeable pump systems that are normally used to deliver a substance through a relatively impermeable catheter.

In a preferred embodiment, the drug release device is an osmotically-driven device. Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like. In one embodiment, the drug release device is an osmotic pump, more particularly an osmotic pump similar to that described in U.S. Pat. No. 5,728,396, e.g., a DUROS™ osmotic pump.

The drug delivery system 100 can further comprise a drug delivery catheter 120, which can be attached to drug delivery device 110 and flow regulator 40 via an attachment element 130 provided at a distal end of delivery conduit 20 of flow regulator 40. The attachment element facilitates permanent or reversible attachment of the catheter to the drug delivery device and/or stabilizes such attachment, e.g., substantially diminish movement of the catheter away from the drug delivery device (e.g., to provide strain relief), so as to reduce risk of breakage of the catheter at the attachment site. The attachment element can be provided as a portion of or component associated with the catheter proximal end, flow regulator delivery conduit, a combination of both, or as a separate element. Any of a variety of attachment elements are suitable for use including, but not limited to, a press fit lock, threaded connector elements, luer lock elements, bayonet connectors, etc.

Flow Regulator as Element of a Drug Delivery Catheter

In one embodiment, the flow regulator is provided as an element of a drug delivery catheter, which catheter is attachable to a drug delivery device. In general, the catheter comprises: 1) a catheter body comprising a proximal end defining a drug inlet, a distal end defining a drug delivery outlet, and a lumen extending between the proximal and distal ends and defining a drug delivery pathway; and 2) a flow regulator for control of drug flow from the drug delivery pathway and into a diversion pathway.

For example, flow regulator can be provided as a component of a drug delivery catheter. In this embodiment, delivery conduit of the flow regulator is positioned within and attached to the body of the catheter in a liquid-tight manner or the delivery conduit and catheter lumen can be formed from a single, continuous element (e.g., are molded or extruded as a single element). The catheter proximal end can be adapted for attachment to drug delivery device as described above.

The catheter body can be any suitable shape including, but not limited to, tubular, elliptical, cylindrical, etc., and may be either smooth on the catheter outer surface, or may comprise ridges (e.g., longitudinal, axial, or circumferential) or other surface variations as will be desirable for the specific applications for which the catheter is used. The catheter body comprises a biocompatible material, more preferably an implantable grade biocompatible material. Exemplary materials include, but are not necessarily limited to, biocompatible polymers, elastomers, metals, metal alloys, glasses, laminates of hydrophilic polymers and hydrophobic polymers, multilaminates or polymer, metals, and/or glasses; and the like.

In general, the catheter and flow regulator can be of any suitable dimension, which can be varied according to the delivery site and other factors. For example, the outer diameter of the catheter body is generally from about 0.01" (about 0.25 mm) to about 0.200" (about 5 mm). The inner diameter of the catheter and of the flow regulator delivery conduit can also be varied as needed, and can range from, for example, about 0.0002" (about 0.005 mm) to about 0.025" (about 5 mm).

The dimensions of the catheter (e.g., inner diameter, outer diameter, wall thickness, etc.) can be substantially the same throughout the length of the catheter, or can be varied. For example, the catheter body can be tapered at the distal end relative to the proximal end, e.g., to facilitate implantation into small and/or delicate structures in the subject and/or to provide a wider proximal end for receiving a drug delivery device. The catheter can comprise a single delivery outlet or a plurality of such delivery outlets. Furthermore, the amount of drug that moves through the multiple delivery outlets can be controlled by one or more flow regulators. Catheters comprising multiple drug delivery outlets can be used to facilitate delivery of drug to multiple treatment sites, and may further be branched to provide for delivery to multiple, specific treatment sites. The catheter can comprise additional elements, such as radiopaque markers to facilitate implantation, a valve at the catheter distal end (e.g., a duckbill valve), a filter positioned within the catheter lumen, etc.

Flow Regulator as Separate Unit

Figure 23:
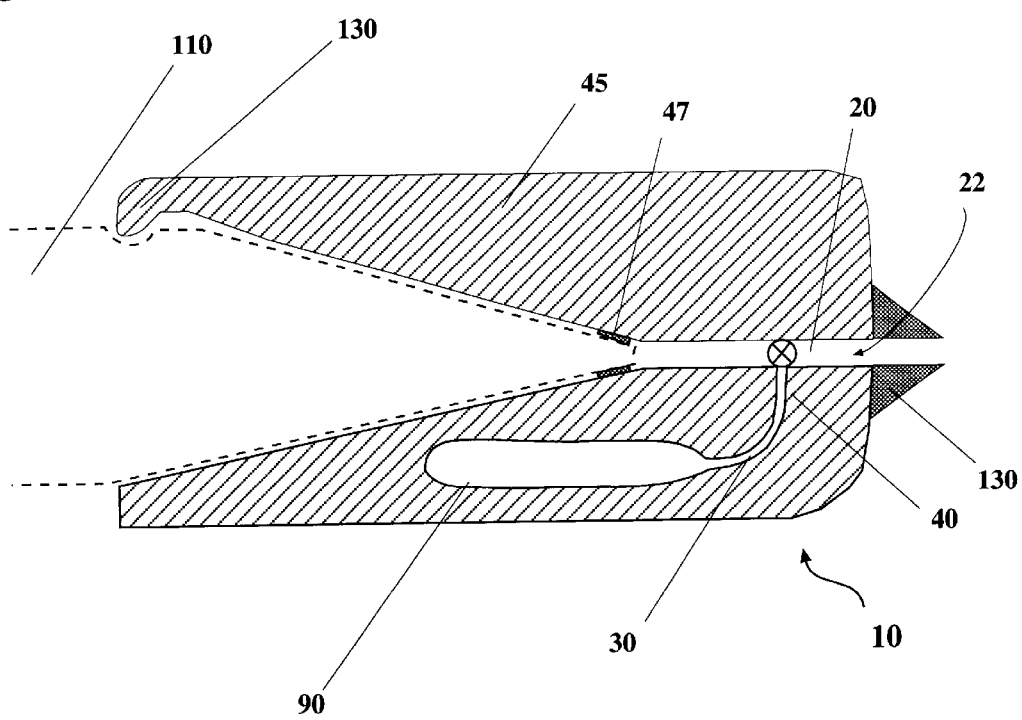
FIG. 23 is cut-away view of a flow regulator 10 provided as a single, attachable unit.

In another embodiment, flow regulator 10 is provided as a separate element that is adapted for attachment to a drug delivery device and, optionally, a drug delivery catheter. In one example illustrated in FIG. 23, flow regulator 10 is provided within housing 45. Drug inlet 21 of delivery conduit 20 is adapted to receive a distal portion of a drug delivery device 110 to provide for flow of drug from the drug delivery device into delivery conduit 20. One or more seals 47 can be positioned within delivery conduit 20 or on an external surface of drug delivery device 110 to facilitate holding drug delivery device 110 in place and/or to provide a liquid-tight seal. Housing 45 can comprise an attachment element (exemplified by a press fit lock in FIG. 23) to facilitate retention of drug delivery device 110 in housing 45. Delivery conduit distal end 22 can be adapted to receive a drug delivery catheter to provide for flow of drug from delivery conduit 22 and into a lumen of the drug delivery catheter. Diversion element 40 of flow regulator 10 is contained with housing 45, with diversion conduit 30 optionally attached to waste reservoir 90. Alternatively, the flow regulator may be adapted to allow for flow of diverted drug directly into a waste reservoir, e.g., without a diversion conduit. All components of flow regulator 10 can be contained within housing 45, as exemplified in FIG. 23, to provide all elements of flow regulator 10 in a single unit. In this embodiment, flow regulator 10 can be provided as a disposable, exchangeable unit that can be adapted for use with a variety of drug delivery devices and drug delivery catheters.

During use, drug flows through delivery pathway 60 from drug reservoir 113 into drug inlet 21, through delivery conduit 20 and, where used, into drug delivery catheter 120 and out catheter distal outlet 122 to a treatment site. Activation of the diversion element 40 of flow regulator 10 results in diversion of drug from delivery pathway 60 and into diversion pathway 70. Where the flow regulator comprises a diversion conduit, diverted drug flows through a diversion pathway defined by the diversion conduit. Optionally, diverted drug can be collected in waste reservoir 90. The dimensions of the flow regulator (e.g., inner diameter of delivery and diversion conduits, dimensions of housing element, etc.) can be varied according to the various drug delivery device and catheters used with the flow regulator, as well as with the application for which the flow regulator is to be used.

Drugs for Delivery Using the Drug Delivery System of the Invention

Any of a wide variety of drugs can be delivered using the drug delivery system of the invention. Drugs suitable for delivery are preferably provided as flowable formulations, and are generally provided as liquids, gels, pastes, or semi-solids. The drugs may be anhydrous or aqueous solutions, suspensions or complexes, and may be formulated with pharmaceutically acceptable vehicles or carriers, as well as additional inert or active ingredients. The drugs of formulations suitable for delivery using the invention may be in various forms, such as uncharged molecules, components of molecular complexes or pharmacologically acceptable salts. Also, simple derivatives of the agents (such as prodrugs, ethers, esters, amides, etc.) that are easily hydrolyzed by body pH, enzymes, etc., can be employed. Preferably the agents are formulated so as to remain stable for long periods of storage on the shelf or under refrigeration, as well as for long periods stored in an implanted drug delivery system of the invention.

Of particular interest is the treatment of diseases or conditions that require long-term therapy, e.g., chronic and/or persistent diseases or conditions for which therapy involves treatment over a period of several days (e.g., about 3 days to 10 days), to several weeks (e.g., about 3 or 4 weeks to 6 weeks), to several months or years, up to including the remaining lifetime of the subject. Subjects who are not presently suffering from a disease or condition, but who are susceptible to such may also benefit from prophylactic therapies using the devices and methods of the invention.

Use of the Flow Regulator in Drug Delivery

The drug delivery system of the invention can be implanted at any convenient site within the subject's body using methods and tools well known in the art, and can be oriented for delivery to any desired treatment site. The devices of the present invention are preferably rendered sterile prior to implantation, which can be accomplished by separately sterilizing each component, e.g., by gamma radiation, steam sterilization or sterile filtration, etc., then aseptically assembling the final system, or by first assembling the system then sterilizing the system using any appropriate method. The final sterilized device may be provided in a package to retain its sterility.

In one embodiment, the drug delivery system of the invention is partially or completely implanted, with at least portion of the drug delivery device retained at an accessible, external or subcutaneous site within the subject's body (e.g., under the skin of the arm, shoulder, neck, back, or leg) or within a body cavity (e.g., within the mouth).

The relative position of the flow regulator can be varied with respect to the subject's body. For example, the portion of the catheter comprising the flow regulator can be maintained at a site external to the subject's body to allow for ready adjustment of the flow regulator, e.g., where the flow regulator comprises a manually adjustable diversion element. Where all or a portion of the flow regulator is maintained at an external site, it may be desirable that the drug delivery system further comprise a waste reservoir for collection of drug that flows through the diversion pathway. In general, a drug delivery outlet (i.e., the delivery outlet or the flow regulator, a drug delivery catheter associated with a flow regulator, or both) is implanted within a subject for delivery of drug to a treatment site.

Figure 24:
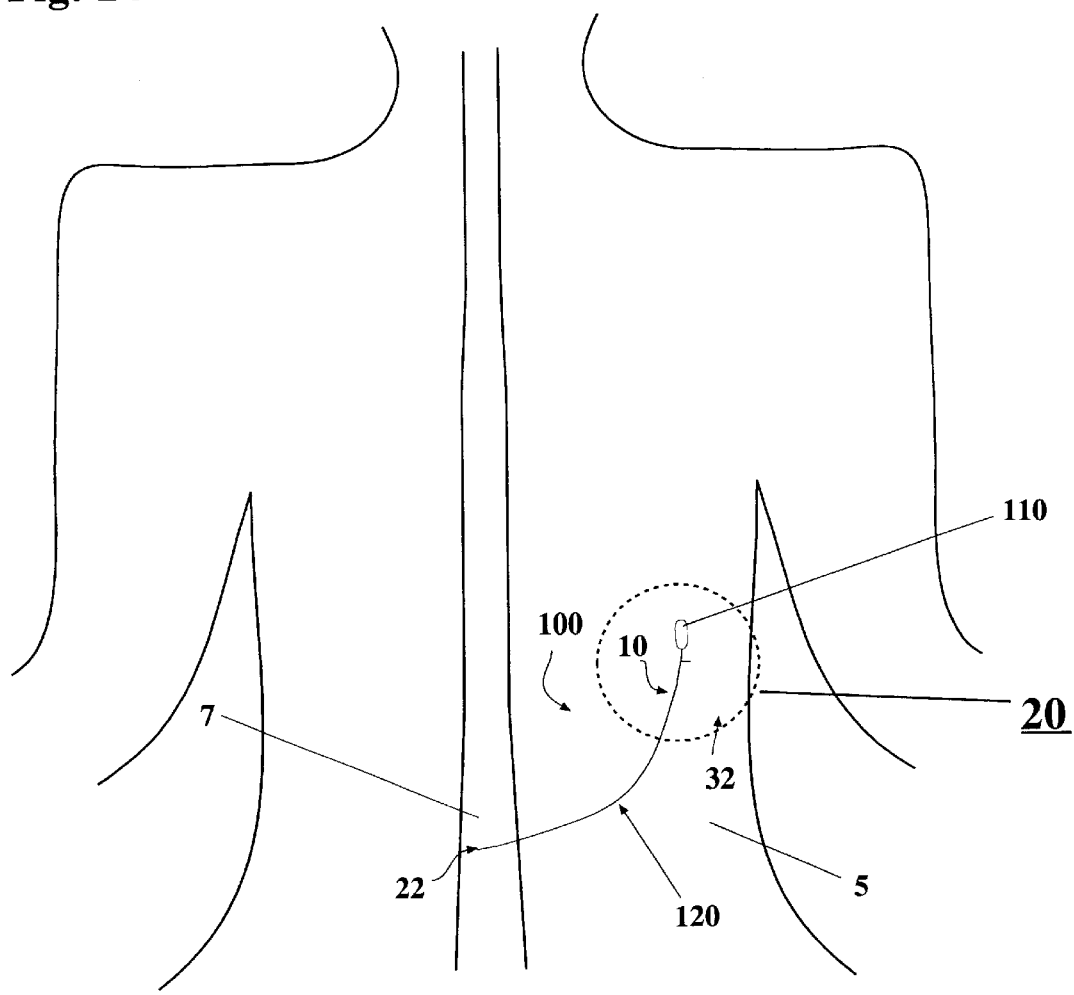
FIG. 24 is a schematic illustrating use of drug delivery system 100 implanted for use in site-specific drug delivery to a treatment site 7, with diverted drug delivered to a systemic site within the subject's body 5.
Figure 25:
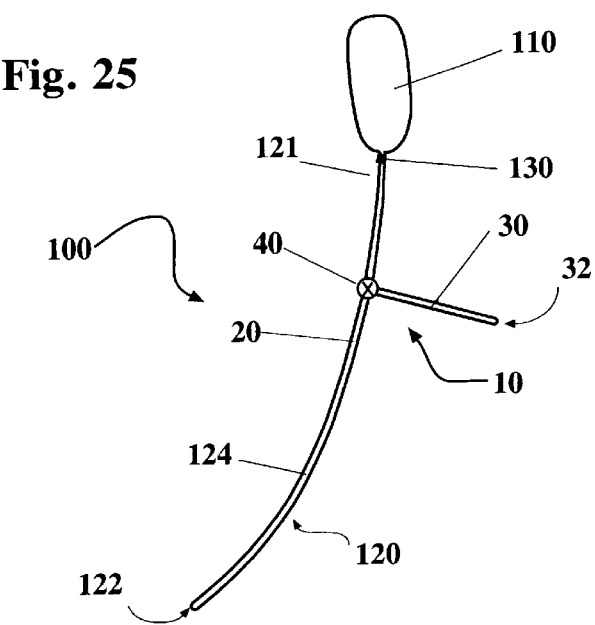
FIG. 25 is a cut-away view of a drug delivery system 100 comprising a drug delivery device 110 attached to a catheter 120, which catheter 120 comprises a flow regulator 10 as an integral component.

In one embodiment exemplified in FIG. 24, a drug delivery outlet 22 is implanted for site-specific drug delivery to a selected treatment site (e.g., within the central nervous system (e.g., an intraspinal site (e.g., an epidural or intrathecal site, site within the brain, etc.)), and the diversion outlet 32 positioned within the body at a site outside the specific treatment site (e.g., at a subcutaneous site or other site external to the specific treatment site that provides for systemic delivery of the diverted waste drug). In this embodiment, drug that flows out the drug delivery outlet 22 is delivered to the selected specific treatment site 7 (e.g., to the spine), while drug that flows out the diversion outlet 32 is delivered systemically in the subject's body 5, where the drug can be safely diluted in the systemic circulation. In an alternative embodiment, diverted drug flows out the delivery conduit proximal drug exit outlet and directly into the systemic circulation, e.g., without flowing through a diversion conduit.

Embodiments that involve delivery of diverted drug to the systemic circulation are particularly attractive where microquantities of drug (e.g., on the order of micrograms per day) are delivered to the specific treatment site, and thus the amount of drug diverted into the diversion conduit and to a systemic site would be even smaller. These embodiments are also attractive where the drug's biological activity is substantially specific for the specific treatment site, and systemic delivery of the drug to the patient would have no substantial, undesirable effect.

Where the drug's biological activity might have undesirable systemic effects, the catheter preferably further comprises a waste reservoir for collection of drug that flows out of the delivery conduit through the diversion pathway. It may be desirable to maintain the waste reservoir at readily accessible site so that waste drug in the waste reservoir can be readily withdrawn, particularly where the subject is to receive therapy for an extended period of time.

The amount of drug delivered to the treatment site is adjusted by manipulation of one or more flow regulators of the drug delivery system. The method of altering an amount of drug administered to a treatment site according to the invention takes advantage of the fact that altering the amount of drug that flows into the diversion pathway alters the amount of drug that flows through the drug delivery outlet. Specifically, where the flow regulator is adjusted to increase the amount of drug that flows out the diversion pathway, the amount of drug delivered through the delivery outlet to the treatment site is proportionately decreased. Likewise, where the flow regulator is adjusted to decrease the amount of drug that flows out the diversion pathway, the amount of drug delivered through the delivery outlet to the treatment site is proportionately increased. For example, the flow regulator can provide for redirection (e.g., into or away from the diversion pathway) of about 0.5% up to 100%, usually about 5% to 90%, normally about 10% to 75% or about 25% to 50% of the drug flow in the drug delivery pathway. The relative amount of drug diverted into the diversion pathway can be selected according to patient need, e.g., developments of side-effects, responsiveness to therapy, etc.

The overall rate of drug delivery through the drug delivery pathway can be adjusted using the flow regulator in a variety of ways. The flow regulator can be set at relative degrees of opening and closing of the drug diversion-pathway and drug delivery pathway. For example, the relative portions of drug flowing through the drug delivery pathway and the diversion pathway can be 90:10, 80:20, 50:50, 25:75, etc. Alternatively, the rate of drug flow can be adjusted by varying the amount of time the drug delivery pathway is open relative to the amount of time the diversion pathway is open. For example, over a given time interval (e.g., seconds, minutes, hours), the ratio of time the drug delivery pathway is open versus the time the diversion pathway is open (delivery:diversion) can be 10:1, 5:1, 3:1, 2:1, 0.5:1, etc.

The invention as shown and described is considered to be the one of the most practical and preferred embodiments. It is recognized, however, that the departures may be made therefrom which are within the scope of the invention and that obvious modifications will occur to one skilled in the art upon reading this disclosure.

What is claimed is:

1. A method for delivering a desired amount of a drug to a localized treatment site of a subject, the method comprising:

causing a therapeutically effective quantity of drug to exit from a drug reservoir of a drug delivery device into a first delivery conduit comprising a first outlet and in a direction toward a localized treatment site; and diverting a portion of the drug exiting the drug delivery device away from the first conduit and into a separate second conduit having a second outlet, wherein drug that flows through the second outlet is delivered to a site within the subject other than a treatment site and away from the localized treatment site such that said diverted portion does not reach the localized treatment site in a therapeutically effective amount;

wherein said diverting results in delivery of a desired amount of drug to the localized treatment site.

2. The method of claim 1, wherein the localized treatment site is a biologically confined treatment site.

3. The method of claim 1, wherein the desired amount of drug is delivered to the localized treatment site by varying the amount of drug diverted from the drug delivery device.

4. The method of claim 1, wherein said diverting is on an intermittent basis.

5. The method of claim 1, wherein the first delivery conduit is suitable for delivery of the drug at a low volume rate.

6. The method of claim 1, wherein the first delivery conduit provides two delivery outlets to provides for delivery of drug to at least two localized treatment sites.

7. The method of claim 1, wherein the localized treatment site is subcutaneous, percutaneous, intravenous, intramuscular, intra-arterial, intravascular, intraperitoneal, intraspinal, epidural, intrathecal, intracranial, intracardial, peritumoral, or intratumoral.

8. The method of claim 1, wherein the localized treatment site is a site within a kidney, liver, pancreas, heart, lung, eye, ear, lymph node, breast, prostate, ovary, testicle, thyroid, spleen, central nervous system, skeletal muscle, bone, lymph vessel, artery, arteriole, capillary bed, blood vessel, vein, peripheral nervous system, digestive system, gastrointestinal tract, urinary bladder, gall bladder, adrenal gland, adipose tissue, parathyroid gland, uterus, fallopian tube, skin, tumorous growth, autologous graft, synthetic graft, or site of microbial infection.

9. The method of claim 1, wherein the drug delivery device is a constant rate drug delivery device.

10. The method of claim 1, where drug diverted from the first conduit is delivered to the subject systemically.

11. The method of claim 1, wherein a distal end of the first drug delivery conduit is attached to a drug delivery catheter, wherein at least the catheter distal end is implanted at the localized treatment site.

12. The method of claim 11, wherein the catheter is adapted for delivery of drug to two localized treatment sites.

13. The method of claim 1, wherein said diverting is provided by adjusting a diversion element, the diversion element being positioned so as to facilitate diversion of flow of drug out of the first conduit and into the second conduit.

14. The method of claim 13, wherein said diverting is by adjusting the diversion element for a first time period so as to facilitate flow through the first conduit, and for a second time period so as to divert flow through the second conduit, wherein varying the length of the first and second time periods results in alteration in the amount of drug delivered to the localized treatment site.

15. The method of claim 13, wherein the diversion element is adjusted so that the delivery conduit and the diversion conduit are each partially open.

16. The method of claim 13, wherein the diversion element is adjusted to simultaneously divert a portion of the drug away from the delivery pathway and toward a site other than a treatment site.

17. The method of claim 1, wherein the localized treatment site is intraspinal, epidural, intrathecal, or intracranial.

18. The method of claim 1, wherein the localized treatment site is intrapericardial.

19. The method of claim 1, wherein the localized treatment site is intratumoral.

20. The method of claim 1, wherein the localized treatment site is within a kidney, liver, pancreas, heart, lung, eye, ear, lymph node, prostate, ovary, testicle, thyroid, spleen, bone, urinary bladder, gall bladder, adrenal gland, parathyroid gland, or uterus.

21. The method of claim 1, wherein the localized treatment site is within the central nervous system.

22. The method of claim 1, wherein drug diverted from the drug delivery pathway is delivered to the subject systemically.

23. A method of controlling an amount of drug administered to a treatment site in a subject with a drug delivery system comprising:
- a flow regulator comprising:
  - a delivery conduit comprising a proximal delivery inlet, a distal delivery outlet, a delivery lumen extending between the proximal delivery inlet and the distal delivery outlet, the delivery conduit lumen defining a delivery pathway, and a diversion element positioned so as to facilitate diversion of flow of drug in a direction away from the delivery pathway, and
  - a diversion conduit comprising a diversion inlet, a diversion outlet, and a diversion lumen extending between the diversion inlet and diversion outlet, the diversion conduit lumen defining a diversion pathway;
- a drug delivery device, wherein the drug delivery device is attached to the flow regulator to facilitate delivery of a drug from the drug delivery device through the delivery conduit lumen and out the distal delivery outlet; and
- a waste reservoir positioned for receiving drug diverted away from the delivery pathway by the diversion element;
- wherein the diversion conduit is in fluid communication with the waste reservoir such that drug diverted away from the delivery pathway by the diversion element flows into the diversion pathway defined by the diversion conduit and into the waste reservoir;
- the method comprising:
  - implanting the drug delivery device;
  - introducing a drug into the flow regulator proximal delivery inlet, said introducing resulting in drug flowing through the drug delivery pathway and to a treatment site in a subject at which a distal end of the drug delivery conduit is implanted; and
  - adjusting the diversion element so that the delivery conduit and the diversion conduit are each partially open, thus diverting a portion of the drug away from the drug delivery pathway such that the diverted portion is delivered into the waste reservoir and does not reach the treatment site in a therapeutically effective amount;
  - wherein said adjusting alters the amount of drug that is delivered to the treatment site in the subject.

24. The method of claim 23, wherein the drug delivery device is a constant rate drug delivery device.

25. The method of claim 23, wherein the distal end of the drug delivery conduit is attached to a drug delivery catheter to provide for extension of the drug delivery pathway to a catheter delivery outlet at the catheter distal end, and wherein the catheter distal end is implanted at the treatment site.

26. The method of claim 25, wherein the catheter is adapted for delivery of drug to two treatment sites.

27. The method of claim 23, wherein the treatment site is subcutaneous, percutaneous, intravenous, intrathecal, intramuscular, intra-arterial, intravascular, intraperitoneal, intrapericardial, intraspinal, epidural, intracranial, intracardial, peritumoral, or intratumoral.

28. The method of claim 23, wherein the treatment site is a site within a kidney, liver, pancreas, heart, lung, eye, ear, lymph node, breast, prostate, ovary, testicle, thyroid, spleen, central nervous system, skeletal muscle, bone, lymph vessel, artery, arteriole, capillary bed, blood vessel, vein, peripheral nervous system, digestive system, gastrointestinal tract, urinary bladder, gall bladder, adrenal gland, adipose tissue, parathyroid gland, uterus, fallopian tube, skin, tumorous growth, autologous graft, synthetic graft, or site of microbial infection.

29. The method of claim 23, wherein the diversion element is adjusted for a first time period so as to facilitate flow through the delivery conduit, and for a second time period so as to divert flow through a diversion element, wherein varying the length of the first and second time periods results in alteration in the amount of drug delivered to the treatment site.

30. A method of administering drug to a treatment site in a subject, the method comprising:
- implanting a flow regulator for use at a treatment site within a subject, wherein the flow regulator comprises:
  - a delivery conduit comprising a proximal delivery inlet, a distal delivery outlet, and a delivery lumen extending between the proximal delivery inlet and the distal delivery outlet, the delivery lumen defining a delivery pathway;
  - a diversion element positioned so as to facilitate diversion of flow of drug in a direction away from the delivery pathway; and
  - a waste reservoir positioned for receiving drug diverted away from the delivery pathway by the diversion element;
- wherein said implanting of the flow regulator comprises implanting at least the distal end of the flow regulator delivery conduit at the treatment site; and
- delivering drug from a drug delivery device, through the drug delivery pathway of the flow regulator, and to the treatment site;
- wherein the drug is administered to the treatment site in the subject and wherein the amount of drug delivered to the treatment site is modulated by adjusting the diversion element of the flow regulator to simultaneously divert a portion of the drug away from the drug delivery pathway such that the diverted portion is delivered to the waste reservoir and does not reach the treatment site in a therapeutically effective amount.

31. A method of controlling an amount of drug administered to a treatment site in a subject with a drug delivery system comprising:
- a flow regulator comprising a delivery conduit comprising a proximal delivery inlet, a distal delivery outlet, a delivery lumen extending between the proximal delivery inlet and the distal delivery outlet, the delivery conduit lumen defining a delivery pathway, and a diversion element positioned so as to facilitate diversion of flow of drug in a direction away from the delivery pathway;
- a drug delivery device, wherein the drug delivery device is attached to the flow regulator to facilitate delivery of a drug from the drug delivery device through the delivery conduit lumen and out the distal delivery outlet; and
- a waste reservoir positioned for receiving drug diverted away from the delivery pathway by the diversion element;
  - the method comprising:
    - implanting the drug delivery device;
    - introducing a drug into the flow regulator proximal delivery inlet, said introducing resulting in drug flowing through the drug delivery pathway and to a treatment site in a subject at which a distal end of the drug delivery conduit is implanted; and
    - adjusting the diversion element of the flow regulator to simultaneously divert a portion of the drug away from the drug delivery pathway and toward a site other than the treatment site such that the diverted portion is delivered into the waste reservoir and does not reach the treatment site in a therapeutically effective amount;

wherein said adjusting alters the amount of drug that is delivered to the treatment site in the subject.

32. The method of claim 30, wherein the drug delivery device is a constant rate drug delivery device.

33. The method of claim 31, wherein the distal end of the drug delivery conduit is attached to a drug delivery catheter, and wherein the catheter distal end is implanted at the treatment site.

34. The method of claim 31, wherein the catheter is adapted for delivery of drug to two treatment sites.

35. The method of claim 31, wherein the treatment site is subcutaneous, percutaneous, intravenous, intrathecal, intramuscular, intra-arterial, intravascular, intraperitoneal, intrapericardial, intraspinal, epidural, intracranial, intracardial peritumoral, or intratumoral.

36. The method of claim 31, wherein the treatment site is a site within a kidney, liver, pancreas, heart, lung, eye, ear, lymph node, breast, prostate, ovary, testicle, thyroid, spleen, central nervous system, skeletal muscle, bone, lymph vessel, artery, arteriole, capillary bed, blood vessel, vein, peripheral nervous system, digestive system, gastrointestinal tract, urinary bladder, gall bladder, adrenal gland, adipose tissue, parathyroid gland, uterus, fallopian tube, skin, tumorous growth, autologous graft, synthetic graft, or site of microbial infection.

37. The method of claim 31, wherein the diversion element is adjusted for a first time periods as to facilitate flow through the delivery conduit, and for a second time period so as to divert flow through a diversion element, wherein varying the length of the first and second time periods results in alteration in the amount of drug delivered to the treatment site.

38. The method of claim 31, wherein the flow regulator further comprises:

a diversion conduit comprising a diversion inlet, a diversion outlet, and a diversion lumen extending between the diversion inlet and diversion outlet, the diversion conduit lumen defining a diversion pathway;

wherein the diversion conduit is in fluid communication with the waste reservoir such that drug diverted by the diversion element flows into the diversion pathway defined by the diversion conduit and into the waste reservoir.

* * * * *